United States Patent [19]

Nemiroff

[11] Patent Number: 4,575,922
[45] Date of Patent: Mar. 18, 1986

[54] METHOD OF FABRICATING INTEGRATED CIRCUITS INCORPORATING STEPS TO DETECT PRESENCE OF GETTERING SITES

[75] Inventor: Michael H. Nemiroff, Del Mar, Calif.

[73] Assignee: Burroughs Corporation, Detroit, Mich.

[21] Appl. No.: 668,512

[22] Filed: Nov. 5, 1984

[51] Int. Cl.[4] .................... H01L 21/265; B01J 17/00
[52] U.S. Cl. ........................................ 29/574; 29/575; 29/576 B; 29/576 T; 148/1.5; 148/187; 250/492.3
[58] Field of Search .................. 29/574, 575, 576 B, 29/576 T; 148/1.5, 187; 250/492.3

[56] References Cited

U.S. PATENT DOCUMENTS

| | | | |
|---|---|---|---|
| 3,984,680 | 10/1976 | Smith | 29/574 |
| 4,021,675 | 5/1977 | Shifrin | 148/1.5 |
| 4,033,787 | 7/1977 | Marshall | 148/1.5 |
| 4,110,625 | 8/1978 | Cairns et al. | 250/492 A |
| 4,332,833 | 6/1982 | Aspnes et al. | 29/574 |
| 4,392,893 | 7/1983 | Du et al. | 148/1.5 |

OTHER PUBLICATIONS

Huff et al. Jour. Electrochem. Soc. 130, Jul. 1983, 1551.

Primary Examiner—Upendra Roy
Attorney, Agent, or Firm—Charles J. Fassbender; Kevin R. Peterson

[57] ABSTRACT

A method of fabricating integrated circuits on a semiconductor substrate includes the steps of directing electromagnetic radiation onto the semiconductor substrate at a small angular offset from the substrate's Bragg angle; measuring the intensity of the radiation that is reflected from the semiconductor substrate at the offset; and continuing with the fabrication of circuits on the substrate only if the measured intensity is substantially larger than the intensity which would reflect at the same angular offset from a defect-free crystal of the substrate material.

12 Claims, 9 Drawing Figures

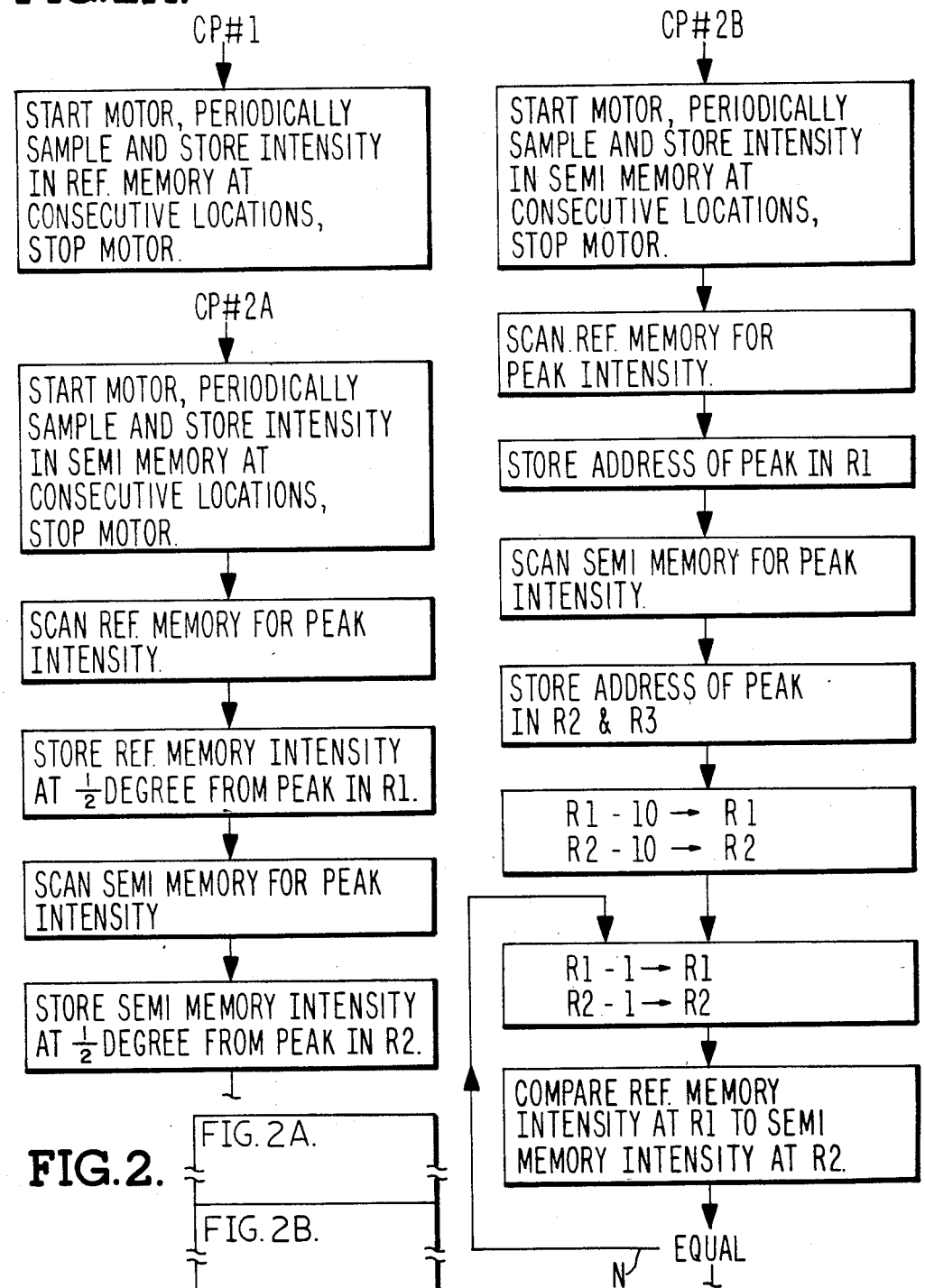

Ar   Ar   Ar   Ar

STAGES AT WHICH THE STEPS OF FIG.2. MAY BE INCORPORATED INTO THE FABRICATION PROCESS.

Vss  INPUT  OUTPUT  V_DD

METHOD OF FABRICATING INTEGRATED CIRCUITS INCORPORATING STEPS TO DETECT PRESENCE OF GETTERING SITES

BACKGROUND OF THE INVENTION

This invention relates to methods of fabricating integrated circuits; and more particularly, it relates to the steps in such method that determine whether or not the substrate on which the integrated circuits are being fabricated contains gettering sites for mobile impurities.

Ideally, the semiconductor substrate on which an integrated circuit is fabricated is made of pure silicon except for a very small amount of P type or N type dopant atoms such as boron or phosphorus. However, in an actual substrate, various other elements are also present in trace quantities as undesirable impurities. For example, traces of copper and iron are typically present.

Such impurities if not dealt with cause the integrated circuit to malfunction. Typically, the impurities ionize and are mobile; and thus they produce undesired currents within the circuit during its operation. To avoid these currents, gettering sites are introduced into the backside of the substrate; and the integrated circuit is then fabricated on the opposite or frontside of the substrate.

A common way to introduce gettering sites into the substrate is to sandpaper the backside surface. This produces a mechanical stress or defects in the substrate's crystal lattice. In turn, this has the effect of creating new allowable energy levels between the conduction band and valance band of the crystal; and these new energy levels act as traps for the mobile impurity ions in the substrate. When a mobile impurity ion migrates in the substrate to a position near the gettering sites, it gets trapped in the new energy levels and thus stops migrating. Consequently, the undesired currents in the circuit stop.

A problem, however, is that heretofore the presence or absence of the gettering sites in the substrate has been difficult if not impossible to detect until after the integrated circuit has been fabricated and tested. Surface texture of the backside surface of a substrate is not a measure of the degree of gettering sites present. A substrate having a rough backside surface can have none or many gettering sites; and the same is true for a substrate having a smooth backside surface.

Consequently, if a purchaser buys semiconductor substrates that are supposed to contain gettering sites, but in fact they do not, the purchaser will not know this until after he fabricates his circuits on the substrates and discovers they fail. But the fabrication of circuitry on a substrate is an expensive and time consuming process.

Accordingly, a primary object of the invention is to provide a method of fabricating integrated circuits which incorporates novel steps for detecting the presence or absence of gettering sites in a substrate.

BRIEF SUMMARY OF THE INVENTION

These objects, and others, are achieved in accordance with the present invention by incorporating into a process for fabricating integrated circuits on a semiconductor substrate the steps of: directing electromagnetic radiation onto the semiconductor substrate at a small angular offset from the substrate's Bragg angle; measuring the intensity of the radiation that is reflected from the semiconductor substrate at the offset; and continuing with the fabrication of the circuits on the semiconductor substrate only if the measured intensity is substantially larger than the intensity which would reflect at the angular offset from a defect-free crystal of the semiconductor substrate.

These steps of directing, measuring, and continuing may be performed prior to the formation of any transistors on the semiconductor substrate; or they may be performed after the formation of transistors on the semiconductor substrate has begun. Suitably, the angular offset at which the radiation is directed is ten to forty minutes; and the electromagnetic radiation has a wavelength of 0.5 Å to 4 Å. Also suitably, the fabrication of circuitry is continued only if the measured intensity is at least 25% larger than that which would reflect from the defect-free crystal.

BRIEF DESCRITPION OF THE DRAWINGS

Various features and advantages of the invention are described in the Detailed Description in conjunction with the accompanying drawings wherein.

DETAILED DESCRIPTION OF THE INVENTION

Figure 1:
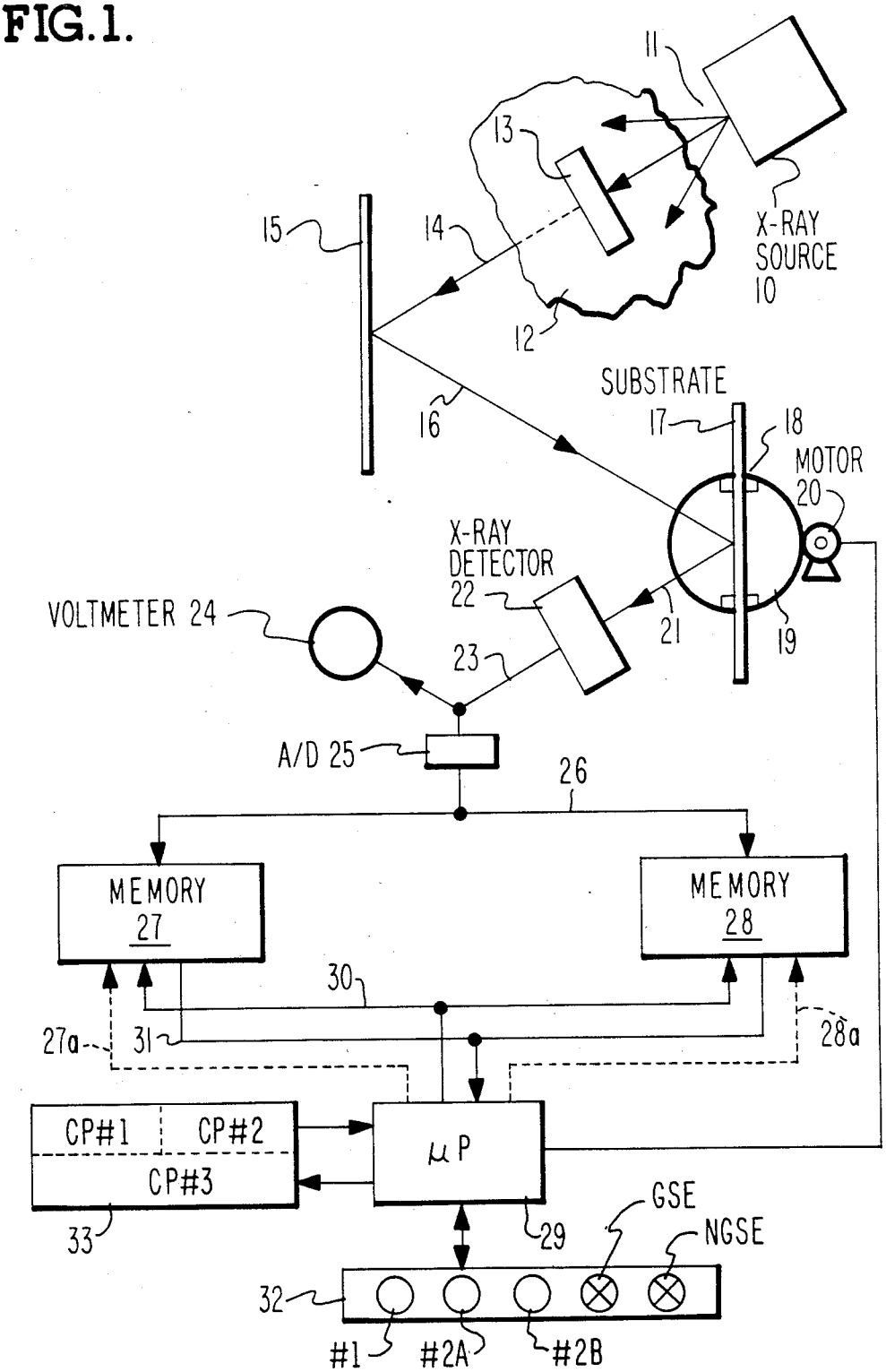
FIG. 1 illustrates an apparatus for carrying out the steps of the present invention.

Referring now to FIG. 1, the details of an apparatus for carrying out the steps of the present invention will be described. This apparatus includes an X-ray source 10 from which X-rays 11 are emitted. Suitably, source 10 is a model XRG 3500 as sold by Philips Electronic Instruments Corporation. Also included is an X-ray collimator 12 having a broad slit 13 through which a portion of the X-rays 11 pass. Suitably, collimator 12 is made of lead; and slit 13 is 1 millimeter by 5 millimeters.

That portion of the X-rays that pass through slit 13 form a beam 14. It is directed against the monochromatic crystal 15 at the Bragg angle $\theta_B$ of the crystal. Angle $\theta_B$ is defined by the mathematical equation $n\lambda = 2d\sin\theta_B$. In this equation, $\lambda$ is the wavelength of the X-rays in beam 14 which is reflected from crystal 15 with the largest intensity; and d is the lattice spacing of the atoms in crystal 15. In other words, crystal 15 operates as a filter which reflects only a certain wavelength in beam 14 as another beam 16.

Beam 16 is directed against another substrate 17. This substrate during one step of the invention is a semiconductor wafer which is being tested to determine whether or not it contains gettering sites for mobile ions. During another step of the invention, substrate 17 is a defect-free crystal of the semiconductor that is being tested.

Substrate 17 is attached by clamps 18 to a gear 19. This gear 19 along with substrate 17 are rotated clockwise by an electric motor 20. Gear 19 and motor 20 are selected such that substrate 17 rotates at a fixed rate of about one to thirty degrees per hour.

Before the rotation of substrate 17 begins, the angle between beam 16 and substrate 17 is manually set to the Bragg angle $\theta_B$ minus a small angular deviation (e.g., 0.1 to 2.0 degrees). Thereafter, substrate 17 is rotated clockwise by gear 19 and motor 20 until the angle which beam 16 makes with substrate 17 increases to the Bragg angle plus a few degrees.

During this rotation, a portion of the X-rays in beam 16 are reflected from wafer 17 as another X-ray beam 21; and an X-ray detector 22 is provided to measure the intensity of beam 21. Suitably, detector 22 is a scintillation detector model #85010100 as sold by Philips Corporation. Such a detector senses X-rays over an angular range of several degrees; and thus it is held stationary as substrate 17 rotates.

Detector 22 generates a signal on an output lead 23 whose magnitude is proportional to the intensity of beam 21. That signal is sent to a voltmeter 24 which provides a visual indication of the magnitude of beam 21. It is used by the operator of the FIG. 1 apparatus to manually set the initial angle which substrate 17 makes with beam 16. Specifically, the operator rotates substrate 17 to the position where voltmeter 24 indicates a maximum signal; and from that position he rotates substrate 17 by the small angular deviation counterclockwise to reach the initial position.

Lead 23 also is coupled to an analog-to-digital converter 25. It has output leads 26 on which digital signals are generated that represent the magnitude of the intensity of beam 21. Signals on the leads 26 are sent to the input terminals of a pair of memories 27 and 28, both of which are addressed by a microprocessor 29 via address lines 30.

Data from the memories 27 and 28 is read by processor 29 over output lines 31. Signals on a set of control lines 27a from processor 29 selectively enable memory 27 to read and write; and signals on another set of control lines 28a from processor 29 selectively enable memory 28 to read and write.

All of the sequences by which the intensity signals on the leads 26 are written into and read from the memories 27 and 28 are controlled by a control panel 32. Panel 32 has three pushbutton switches labeled #1, #2a, and #2b. When button #1 is pushed, processor 29 executes a control program CP#1 in a memory 33; when button #2a is pushed, processor 29 executes another control program CP#2a; and when button #2b is pushed, processor 29 executes another control program CP#2b.

Each control program will now be described in detail in conjunction with FIG. 2. Consider first program CP#1. In general, its function is to load memory 27 with the intensity signals on the leads 26 while a defect-free crystal 17 is rotated about the Bragg angle by gear 19 and motor 20.

Prior to pushing button #1, an operator must place the crystal in the clamps 18 and position it at an angle that is a small amount less than the Bragg angle by utilizing voltmeter 24 as described above. Thereafter, when button #1 is pushed, processor 29 sends a signal to motor 20 which starts the motor and thereby causes substrate 17 to rotate clockwise at a fixed rate. As this rotation occurs, processor 29 periodically sends control signals on the leads 27a which cause memory 27 to store the intensity signals on the leads 26 at consecutive memory locations.

Preferably, at least six hundred samples are stored in memory 27 for each degree of rotation of substrate 17. These samples continue to be taken until the angle between beam 16 and substrate 17 increases to several degrees beyond the Bragg angle. Then processor 29 sends another signal to motor 20 which turns it off.

Consider now the details of control program CP#2a. For this program to operate, the semiconductor wafer that is to be tested for gettering sites must be held by the clamps 18 and positioned at the Bragg angle minus a small deviation. Thereafter, when button #2a is pressed, processor 29 starts motor 20 which causes substrate 17 to rotate clockwise at a fixed rate.

As this rotation occurs, processor 29 periodically sends control signals on the leads 28a which cause memory 28 to store the intensity signals on the leads 26 at consecutive memory locations. Preferably, these intensity signals are stored at the same rate in memory 28 that they were stored by control program CP#1 in memory 27. Then, after substrate 17 has rotated about one degree past the Bragg angle, processor 29 sends a signal to motor 20 which causes it to turn off.

Next, processor 29 scans the intensity signals in memory 27 to find the peak intensity. This is achieved via processor 29 by sending consecutive memory addresses on the leads 30 along with read commands on the control leads 27a, and reading and comparing the intensity signals from memory 27 on the leads 31 until the maximum intensity is found.

Then processor 29 takes the address in memory 27 at which the peak intensity occurs and adds an increment to it to thereby generate the address in memory 27 of the intensity that was stored when the angle between beam 16 and wafer 17 was ten to thirty minutes from the Bragg angle. For example, if wafer 17 is rotated at a rate of ten degrees per hour and six hundred samples are taken per hour, then an increment of ten to thirty is added to the address of the peak intensity. That intensity in memory 27 at the incremented address is then stored in processor 29 in a register R1.

Similar steps are performed by processor 29 on the intensity samples that are stored in memory 28. That is, processor 29 first scans the intensities in memory 28 to determine the address of the peak that is there stored; then it increments the address of the peak intensity to obtain the address of the intensity that is ten to thirty minutes from the peak; and then it stores the intensity at the incremented address in a register R2.

Next, processor 29 compares the two intensities in registers R1 and R2. If the intensity in register R2 is substantially larger than the intensity in register R1, then processor 29 sends a signal to control panel 32 which illuminates a lamp GSE which indicates that gettering sites exist. Preferably, the intensity in register R2 is at least 25% larger than the intensity in register R1 for this to occur. In response, the processor of fabricating integrated circuits on substrate 17 is continued.

Conversely, if the intensity in register R2 is not substantially larger than the intensity in register R1, then processor 29 sends a signal to control panel 32 which illuminates a lamp NGSE which indicates no gettering sites exist. In response, wafer 17 is either discarded, or wafer 17 is cycled through another process which introduces gettering sites into the wafer. Then this modified wafer is used in the process in which the integrated circuits are fabricated.

Figure 3:
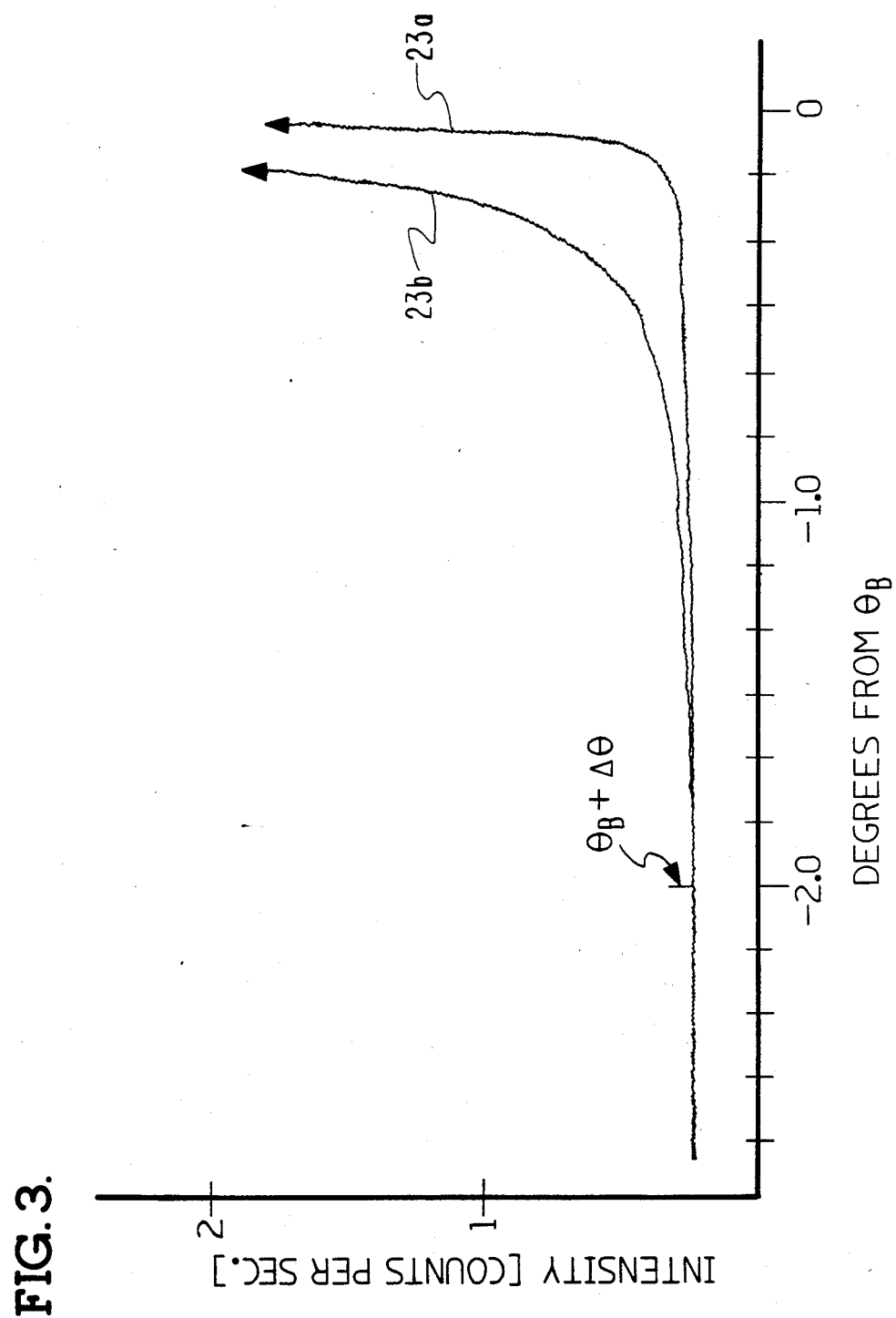
FIG. 3 illustrates the intensities of a reflected X-ray beam which the FIG. 1 apparatus measures.

To understand the theory on which control programs CP#1 and CP#2 are based, reference should now be made to FIG. 3. It contains a pair of curves 23a and 23b that represent the signals that occur on line 23 as these control programs are executed. Curve 23a occurs when control program CP#1 is executed; and either one of the curves 23a or 23b occurs during the execution of control program CP#2a.

In FIG. 3, the angle between beam 16 and substrate 17 is plotted on the horizontal axis as an angular deviation from the Bragg angle $\theta_B$; and the intensity signal on line 23 is plotted on the vertical axis. If substrate 17 is a defect-free crystal, then as curve 23a shows, its intensity is very high at the Bragg angle and it drops off rapidly with only a very small angular deviation from the Bragg angle (e.g., an angular deviation of less than ten seconds).

By comparison, if substrate 17 has defects in its crystal lattice that are randomly distributed near the substrate surface (i.e., within 50 microns of the surface), then the intensity of the X-rays that are reflected from it falls off less rapidly than curve 23a. Thus, in the range of ten to thirty minutes from the Bragg angle, intensity 23b is at least 25% larger than intensity 23a.

Returning now back to FIG. 2, the details of control program CP#2b will be described. For this program to operate, the semiconductor wafer that is to be tested for gettering sites must also be held by the clamps 18 and positioned at the Bragg angle minus a small deviation. Thereafter, when button #2b is pressed, processor 29 starts motor 20 which causes substrate 17 to rotate clockwise.

As this rotation occurs, processor 29 periodically sends control signals on the leads 28a which cause memory 28 to store the intensity signals on the leads 26 at consecutive memory locations. Thereafter, when substrate 17 has rotated several degrees past the Bragg angle, processor 29 sends a signal to motor 20 which causes it to turn off.

Next, processor 29 reads and compares the intensity signals in memory 27 to find the peak intensity. Then it stores the address in memory 27 of the peak intensity in a register R1. Processor 29 then reads and compares the intensity signals in memory 28 to find the peak intensity that is there stored. Then it stores the memory 28 address of the peak intensity in two registers R2 and R3.

Next, processor 29 decrements the address in registers R1 and R2 by a predetermined amount to obtain the addresses of the peak intensities minus about ten minutes. At those addresses, the stored intensities are certain to be unequal if the substrate which is under test contains gettering sites.

Thereafter, processor 29 decrements by one the addresses in registers R1 and R2, and compares the intensities that are stored in memories 27 and 28 at those addresses. This decrement and compare operation continues until the intensities at the R1 and R2 addresses are equal. By equal is herein meant that any difference between the two intensities is within some predetermined minimum value.

Next, processor 29 computes the maximum strain S that occurs in the substrate 17 that is being tested for gettering sites by the formula $S = \text{SIN}\theta_B \div (\text{SIN}\theta_B + \Delta\theta) - 1$. In this formula $\theta_B$ is the Bragg angle, and $\Delta\theta$ is the smallest angular offset from $\theta_B$ at which the intensities in memories 27 and 28 are equal. Offset $\Delta\theta$ is computed by subtracting the addresses in registers R2 and R3, and multiplying the difference by the angular movement of substrate 17 which occurs between each intensity sample that is stored in memory 28.

Processor 29 then compares the computed maximum strain S to a predetermined limit, (e.g., 0.010 or 1%). If that limit is exceeded, then processor 29 sends a signal to control panel 32 which illuminates lamp GSE; and in response thereto, the fabrication of circuitry on the substrate 17 that is being tested continues. Conversely, if the maximum strain S is less than the limit, then processor 29 sends a signal to control panel 32 which illuminates lamp NGSE; and in response, the substrate that is being tested is either discarded, or gettering sites are introduced into it and then the fabrication of circuitry on it continues.

In order to understand the theory on which control program CP#2b is based, the following equations 1-6 are provided:

$$S = \frac{\Delta d}{d} = \frac{d' - d}{d} \qquad \text{eq. 1}$$

$$n\lambda = 2d\,\text{SIN}\theta_B = 2d'\text{SIN}\theta_{B'} \qquad \text{eq. 2}$$

$$d' = \frac{d\,\text{SIN}\theta_B}{\text{SIN}\theta_{B'}} \qquad \text{eq. 3}$$

$$S = \frac{\frac{d\,\text{SIN}\theta_B}{\text{SIN}\theta_{B'}} - d}{d} = \frac{\text{SIN}\theta_B}{\text{SIN}\theta_{B'}} - 1 \qquad \text{eq. 4}$$

$$\theta_{B'} = \theta_B + \Delta\theta \qquad \text{eq. 5}$$

$$S = \frac{\text{SIN}\theta_B}{\text{SIN}(\theta_B + \Delta\theta)} - 1 \qquad \text{eq. 6}$$

Equation 1 gives a definition of strain. In it, the term d is the lattice spacing of the atoms of an unstrained crystal, and the term d' is the lattice spacing of the atoms of a strained crystal.

Equation 2 is the Bragg equation as it applies to both a strained and an unstrained crystal. In it, the term $\theta_B$ is the Bragg angle for an unstrained crystal lattice, and the term $\theta_{B'}$ is the Bragg angle for a strained crystal lattice.

By utilizing equation 2, the term d' can be written in terms of d, $\theta_B$ and $\theta_{B'}$. This is given as equation 3. Then, by substituting equation 3 into equation 1, a new equation 4 is obtained which expresses strain in terms of d, $\theta_B$, and $\theta_{B'}$.

Figure 2B:
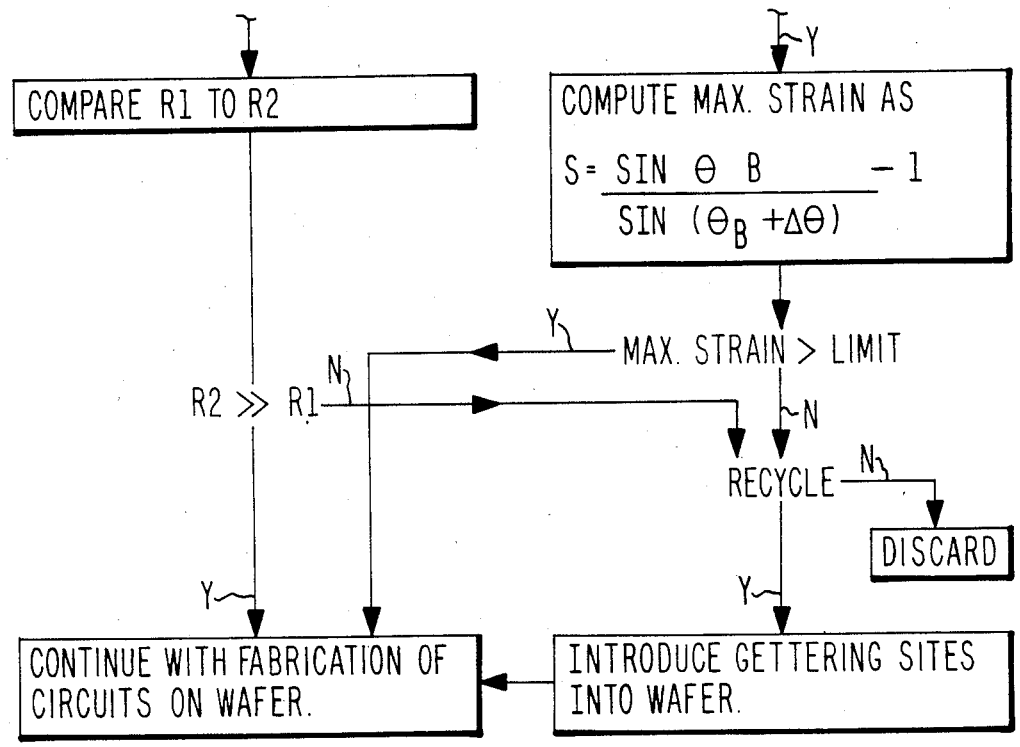
FIG. 2 illustrates a flow chart of several control programs which the FIG. 1 apparatus executes.

$\theta_{B'}$ can also be expressed, as by equation 5, in terms of $\theta_B$ and the angular deviation $\Delta\theta$ from $\theta_B$ at which the curves 23a and 23b in FIG. 2 converge. Then, substituting equation 5 into equation 4 yields equation 6 which is the equation for maximum strain.

One feature of the invention is that the FIG. 2 steps can be carried out at any stage of an integrated circuit fabrication process. This is because the X-ray beam 16 is non-destructive to any circuitry which is fabricated or partially fabricated on the substrate 17.

FIGS. 4a-4f show some specific stages in an exemplary IC fabrication process at which the steps of the present invention may be performed. These figures are taken from U.S. Pat. No. 4,354,307 which is assigned to Burroughs Corporation and which describes a method of mass producing miniature field effect transistors in high density LSI/VLSI chips.

Figure 4A:
FIGS. 4a–4f illustrate a method of fabricating integrated circuits and several stages in that method at which the steps of FIG. 2 are performed.
Figure 4B:
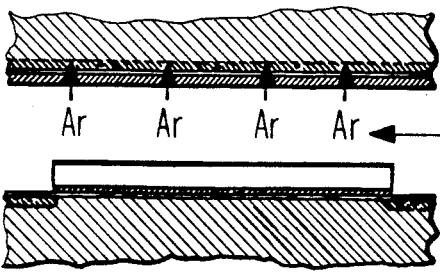
Figure 4C:
Figure 4D:
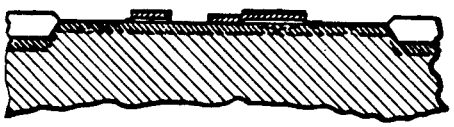
Figure 4E:

FIG. 4a illustrates a step in which argon atoms are implanted into a backside surface of a substrate in order to there produce gettering sites; but as explained in the background of this disclosure, sandpapering the surface may also be used to produce gettering sites. In any case, if gettering sites are introduced by a vendor of the substrate, and the remaining steps 4b-4f are performed by a purchaser of the substrate, it is very important that the purchaser be able to determine whether or not the gettering sites do in fact exist. This determination is made in accordance with the invention by the above described process steps of FIG. 2.

Alternatively, one may prefer to perform the steps of the present invention after some high temperature steps of the IC fabrication process have been completed. During a high temperature step, gettering sites tend to dissipate; and any such dissipation can be detected by subsequently performing the steps of FIG. 2. For example, the steps of FIG. 2 may be performed after the steps of FIGS. 4a–4c during which the substrate is heated to temperatures of 1,000° C.

Figure 4F:
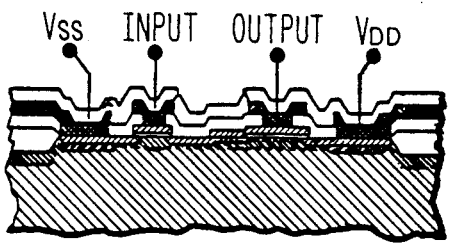

As another alternative, the steps of the present invention may be carried out after the fabrication of the entire integrated circuit is complete (e.g., after the step of FIG. 4f). Checking for the presence of gettering sites even at this late stage in the process via the steps of FIG. 2 will not adversely affect the circuitry on the substrate.

Various preferred methods of fabricating integrated circuits in accordance with the present invention have now been described in detail. In addition, however, several changes and modifications can be made to these details without departing from the nature and the spirit of the invention. Accordingly, it is to be understood that the invention is not limited to said details but is defined by the appended claims.

What is claimed is:

1. For use in fabricating integrated circuits on a semiconductor substrate, a method including the steps of:
   directing electromagnetic radiation onto said semiconductor substrate at a small angular offset from the substrate's Bragg angle;
   measuring the intensity of the radiation that is reflected from said semiconductor substrate at said offset; and
   fabricating said circuits on said semiconductor substrate only if the measured intensity is substantially larger than the intensity which would reflect at said angular offset from a defect-free crystal of said semiconductor substrate.

2. A method according to claim 1 and further including the steps of:
   generating gettering sites for mobile ions in said semiconductor substrate if said measured intensity is not substantially larger than that which would reflect from said defect-free crystal; and thereafter
   fabricating said circuits on said semiconductor substrate as modified with said gettering sites.

3. A method according to claim 1 and further including the step of:
   discarding said semiconductor substrate if said measured intensity is not substantially larger than that which would reflect from said defect-free crystal.

4. A method according to claim 1 wherein all of the recited steps are performed prior to the formation of any transistors on said semiconductor substrate.

5. A method according to claim 1 wherein all of the recited steps are performed after the formation of transistors on said semiconductor substrate has begun.

6. A method according to claim 1 wherein said angular offset is ten to forty minutes.

7. A method according to claim 1 wherein said radiation has a wavelength of 0.5 Å to 4 Å.

8. A method according to claim 1 wherein said semiconductor material is selected from silicon, germanium and gallium arsenide.

9. A method according to claim 1 wherein said fabricating step is performed only if said measured intensity is at least 25% larger than that which would reflect from said defect-free crystal.

10. In a process for fabricating integrated circuits on a semiconductor substrate, the substeps of:
    directing electromagnetic radiation onto said semiconductor substrate at a small angular offset of ten to forty minutes from the Bragg angle of said substrate; and
    continuing with the fabricating of said circuits on said semiconductor substrate only if at said angular offset, the radiation reflected therefrom exceeds by a predetermined amount the radiation which a defect-free crystal of said substrate would reflect at the same offset.

11. A process according to claim 10 wherein the fabricating of said circuits is continued only if the radiation reflected from said semiconductor substrate is at least 25% larger than the radiation which said defect-free crystal would reflect.

12. A process according to claim 10 wherein the fabricating of said circuits is continued only if the maximum stress in said semiconductor substrate as calculated by $S = \mathrm{SIN}\theta_B \div \mathrm{SIN}(\theta_B + \Delta\theta) - 1$ exceeds a predetermined minimum value, where $\theta_B$ is the Bragg angle and $\Delta\theta$ is the smallest angular offset from $\theta_B$ at which the radiation from said semiconductor substrate and said defect-free crystal converge.

* * * * *